United States Patent [19]
Whitney et al.

[11] Patent Number: 6,107,477
[45] Date of Patent: Aug. 22, 2000

[54] NON-OPTIMAL KOZAKS SEQUENCES

[75] Inventors: Michael A. Whitney, La Jolla; Edward M. Rockenstein, Chula Vista, both of Calif.

[73] Assignee: Aurora Biosciences Corporation, San Diego, Calif.

[21] Appl. No.: 09/167,040

[22] Filed: Oct. 6, 1998

Related U.S. Application Data

[63] Continuation-in-part of application No. PCT/US97/17395, Sep. 26, 1997, which is a continuation-in-part of application No. 08/719,697, Sep. 26, 1996, Pat. No. 5,928,888.

[51] Int. Cl.$^7$ .......................... C07H 21/04; C07H 21/02; C12N 1/21; C12N 15/79; C12N 15/74
[52] U.S. Cl. .......................... 536/24.1; 536/23.1; 536/24.2; 435/252.3; 435/320.1; 435/325
[58] Field of Search .................................. 536/23.1, 24.1, 536/24.2; 435/320.1, 325, 252.3

[56] References Cited

PUBLICATIONS

Hazel et al. A gene inducible by serum growth factors encodes a member of the steroid and thyroid hormone receptor superfamily. Proc. Natl. Acad. Sci. USA. vol. 85, pp. 8444–8448, Dec. 1988.
Ryseck et al. Structure, mapping and expression of a growth factor inducible gene encoding a putative nuclear hormonal binding receptor. The EMBO Journal, vol. 8, pp. 3327–3335, Aug. 1989.
Sharma et al. Multiple control elements for the uvrC gene unit of *Escherichia coli*. vol. 14, pp. 2301–2317, Feb. 1986.
Dinesh–Kumar SP et al., Plant Cell 1993 Jun.; 5(6): 679–92.
Kozak M, Mol Cell Biol 1988 Jul.; 8(7) 2737–44.
Kozak M, Mol Cell Biol 1989 Nov.; 9(11): 5134–42.
Kozak M, Cell 1986 Jan. 31; 44(2): 283–92.
Kozak M, Nucleic Acids Res 1990 May 11; 18(9): 2828.
Kozak M, J Biol Chem 1991 Oct. 25; 266(30): 19867–70.
Kozak M, et al. Annu Rev Cell Biol 1992; 8: 197–225.
Kozak M, J Mol Biol 1994 Jan 7; 235(1): 95–110.
Kozak M, Proc Natl Acad Sci USA 1995 Mar. 28; 92(7); 2662–6.
Kozak M, J Mol Biol 1987 Aug. 20; 196(4): 947–50.
Kozak M, Nucleic Acids Res 1987 Oct. 26; 15(20): 8125–48.
Kozak M, Proc Natl Acad Sci USA 1986 May; 83(9): 2850–4.
McBratney et al., Mol Cell Biol 1996 Jul.; 16(7):3523–34.
Roner MR et al., Proc Natl Acad Sci USA 1993 Oct. 1, 90(19): 8947–51.
Sagliocco FA et al., J Biol Chem 1993 Dec. 15;268(35): 26522–30.
Schuster–Gossler K et al., Dev Dyn 1998 Jun; 212(2): 214–28.

*Primary Examiner*—Stephanie W. Zitomer
*Assistant Examiner*—Cynthia Wilder
*Attorney, Agent, or Firm*—Gray Cary Ware & Freidenrich LLP; Lisa A. Haile

[57] ABSTRACT

A non-optimal translational start site (Kozak) polynuclcotide sequence as set forth in SEQ ID NO:2 is provided. An expression vector for expressing a protein of interest, utilizing the non-optimal translational start site is also provided. Host cells containing the expression vector utilizing the non-optimal translational start site are also provided. A selectable marker encoded by a nucleic acid sequences utilizing the non-optimal translational start site is further provided.

20 Claims, 3 Drawing Sheets

```
                              SEQUENCE LISTING

<160> NUMBER OF SEQ ID NOS: 2

<210> SEQ ID NO 1
<211> LENGTH: 13
<212> TYPE: DNA
<213> ORGANISM: Eukaryote
<220> FEATURE:
<221> NAME/KEY: misc_feature
<222> LOCATION: (0)...(0)
<223> OTHER INFORMATION: optimal translational start site of eukaryotic
      mRNA
<220> FEATURE:
<221> NAME/KEY: misc_feature
<222> LOCATION: (0)...(0)
<223> OTHER INFORMATION: r = G or A

<400> SEQUENCE: 1
tccgccrcca tgg                                                        13

<210> SEQ ID NO 2
<211> LENGTH: 15
<212> TYPE: DNA
<213> ORGANISM: Eukaryote
<220> FEATURE:
<221> NAME/KEY: misc_feature
<222> LOCATION: (0)...(0)
<223> OTHER INFORMATION: non-optimal translational start site of
      eukaryotic mRNA

<400> SEQUENCE: 2
agatctttat ggacc                                                      15
```

NON-OPTIMAL KOZAKS SEQUENCES

CROSS REFERENCE TO RELATED APPLICATIONS

This application claims priority to the following patent applications: the present application is a continuation-in-part of Patent Cooperative Treaty application No. PCT/US97/17395, filed Sep. 26, 1997, which is a continuation-in-part of U.S. patent application Ser. No.: 08/719,697, filed Sep. 26, 1996 now U.S. Pat. No. 5,928,888, each of which is incorporated herein by reference.

FIELD OF THE INVENTION

The present invention is generally related to regulatory sequences and more specifically to sequences which regulate the start of translation.

BACKGROUND OF THE INVENTION

The genetic information of the cell is stored and transmitted in the nucleotide sequence of the deoxyribonucleic acid (DNA). Expression of this information requires transcription of DNA into messenger ribonucleic acid (mRNA) molecules that carry specific and precise information to the cytoplasmic sites of protein synthesis. In eukaryotic cells the mRNA are synthesized in the nucleus, often as larger precursor molecules called heterogenous nuclear RNA (hnRNA).

The mRNA in the cytoplasm has several identifying characteristics. In eukaryotic cells, mRNA is usually a monocistronic, and encodes only one polypeptide. The 5' end is capped with a specific structure involving 7-methylguanosine linked through a 5'-triphosphate bridge to the 5' end of the messenger sequence. A 5'-non-translated region, which may be quite short or hundreds of nucleotides in length, separates the cap and the translational start site, which contains an AUG codon. The leader sequences of most vertebrate mRNAs are 20 to 100 nucleotides in length. Usually the translational start site is the first AUG sequence encountered as the message is read from the 5' to the 3' end. The informational sequences that encode a polypeptide are then contiguous with the initiation signal. The polypeptide-encoding sequences continue until a specific translational termination site is reached, which is followed by a 3' untranslated sequence of about 100 nucleotides in length, before the mRNA terminates in a polyadenylate tail.

Prokaryotic mRNA differs from eukaryotic mRNA in a few details. The 5' terminus is not capped, but retains a terminal triphosphate from initiation of its synthesis by an RNA polymerase. Most of the mRNA are polycistronic, encoding several polypeptides, and can include more than one initiation AUG sequence. In each case a ribosome-positioning sequence is located about 10 nucleotides upstream of the AUG initiation signal. An untranslated sequence follows the last coding sequence, but there is no polyadenylate tail.

The translational start site of eukaryotic mRNA is also called a Kozak sequence (Kozak, M., 1987, Nucl. Acid Res. 15(20):8125–8148, herein incorporated by reference). An optimal Kozak sequence has the form of:

(TCC) GCC (A/G)CC <u>ATG</u> G (SEQ ID NO:1)

The most highly conserved position in this motif is the purine (which is most often an A) three nucleotides upstream of the ATG codon, which indicates the start of translation (Kozak, M., 1987, J. Mol. Biol. 20:947–950, herein incorporated by reference). Upstream ATG codons occur in fewer than 10% of vertebrate mRNAs, a notable exception of which are oncogene transcripts (Kozak, M., 1987, Nucl. Acids Res. 15:8125–8148). Both naturally occurring and synthetic translational start sites of the Kozak form can be used in the production of polypeptides by molecular genetic techniques (Kozak, M., 1996, Mamm. Genome 7:563–574).

SUMMARY OF THE INVENTION

A polynucleotide containing a non-optimal translational start site, having a sequence as set forth in SEQ ID NO:2, is provided.

AGATCTTTATGGACC (SEQ ID NO:2)

In one aspect of the present invention, an expression vector for expressing a protein of interest, comprising a nucleic acid encoding a gene of interest with a translational initiation start site of the gene of interest having the sequence of SEQ ID NO:2 is provided. A host cell containing an expression vector for expressing of a protein of interest, comprising a nucleic acid encoding a gene of interest with a translational initiation start site of the gene of interest having the sequence of SEQ ID NO:2, is also provided.

In another aspect of the present invention, a selectable marker encoded by a nucleic acid sequence, wherein a translation initiation start site of said sequence is encoded by SEQ ID NO:2 is further provided.

BRIEF DESCRIPTION OF THE DRAWINGS

FIG. 2 shows the FACS analysis of a population of genomically BLEC integrated clones. Individual cells are plotted by fluorescent emission properties at 400 nm excitation. The x-axis represents green emission (530 nm). The y-axis represents blue emission (465 nm). Cells with a high blue/green ratio will appear blue in color and cells with a low blue/green ratio will appear green in color.

DESCRIPTION OF THE PREFERRED EMBODIMENTS

It must be noted that as used herein and in the appended claims, the singular forms "a", "and", and "the" include plural referents unless the context clearly dictates otherwise. Thus, for example, reference to "a target cell" includes a plurality of such cells and reference to "the expression vector" includes reference to one or more transformation vectors and equivalents thereof known to those skilled in the art, and so forth.

Unless defined otherwise, all technical and scientific terms used herein have the same meaning as commonly understood to one of ordinary skill in the art to which this invention belongs. Although any methods, cells and genes similar or equivalent to those described herein can be used in the practice or testing of the invention, the preferred methods, devices and materials are now described.

All publications mentioned herein are incorporated herein by reference in full for the purpose of describing and disclosing the cell lines, vectors, and methodologies which are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The present invention provides a non-optimal translational start site (Kozak) polynucleotide having a sequence:

AGATCTTT<u>ATG</u>GACC (SEQ ID NO:2)

wherein the underlined ATG is a codon encoding methionine, the so-called start codon.

The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g. a cDNA) independent of other sequences. The nucleotides of the invention can be ribonucleotides, deoxyribonucleotides, or modified forms of either nucleotide. The term includes single and double forms of DNA. When the sequence is RNA, the deoxynucleotides A, G, C, and T of SEQ ID NO:1 are replaced by ribonucleotides A, G, C, and U, respectively.

The non-optimal translational start site of the invention can be used to initiate the translation of any nucleotide sequence of interest. By "nucleotide sequence of interest" is meant any nucleotide sequence (DNA, RNA, or both DNA and RNA). The nucleotide sequence of interest may encode a protein or other molecule that is desirable for expression in a target cell (e.g., for production of the protein or other biological molecule (e.g., a therapeutic cellular product) in the target cell). The nucleotide sequence of interest is generally operatively linked to other sequences which are needed for its expression, e.g., a promoter. Use of "DNA of interest" throughout the specification is not meant to limit the invention to deoxyribonucleic acid.

A "gene product of interest" is a polypeptide, RNA molecule, or other gene product that is desired for expression in the subject. "Gene products of interest" can include, for example, polypeptides that serve as marker proteins to assess cell transformation and expression, fusion proteins, polypeptides having a desired biological activity, gene products that can complement a genetic defect, RNA molecules, transcription factors, and other gene products that are of interest in regulation and/or expression. "Gene products of interest" include nucleotide sequences that provide a desired effect or regulatory function (e.g., transposons, transcription factors, introns, splice signals, etc.). Examples of gene products of interest include, but are not limited to: hormone receptors (e.g. mineralcorticosteroid, glucocorticoid, and thyroid hormone receptors); intramembrane proteins (e.g. TM-1 and TM-7) intracellular receptors (e.g., orphans, retinoids, vitamin D3 and vitamin A receptors); signaling molecules (e.g., kinases, transcription factors, or molecules such signal transducers and activators of transcription) (*Science* Vol. 264, 1994, p.1415–1421; *Mol. Cell Biol.*, Vol. 16, 1996, p.369–375); receptors of the cytokine superfamily (e.g. erthyropoietin, growth hormone, interferons, and interleukins (other than IL-8) and colony-stimulating factors); G-protein coupled receptors, see U.S. Pat. No. 5,436,128 (e.g., for hormones, calcitonin, epinephrine, gastrin, and paracrine or autocrine mediators, such as stomatostatin or prostaglandins) and neurotransmitter receptors (norepinephrine, dopamine, serotonin or acetylcholine); tyrosine kinase receptors (such as insulin growth factor, nerve growth factor (U.S. Pat. No. 5,436,128)).

A "therapeutic gene product" is a polypeptide, RNA molecule or other gene product that, when expressed in a target cell, provides a desired therapeutic effect, e.g., ablation of an infected cell, expression of a polypeptide having a desired biological activity, and/or expression of an RNA molecule for antisense therapy (e.g., regulation of expression of a endogenous or heterologous gene in the target cell genome). For example, Goldsmith et al, WO 90/07936, described a system for ablating specific cells within a tissue by using a promoter that is activated only in that tissue to express a therapeutic gene product only in the desired cells. For example, in a patient about to receive a heterologous transplant or graft, one may administer a polynucleotide encoding a toxin to T cells targeting the graft.

A selectable marker is one type of gene product of interest. A "selectable marker" is a gene sequence or a protein encoded by that gene sequence. Expression of the protein encoded by the selectable marker allows a host cell transfected with an expression vector which includes the selectable marker to be easily identified from a host cell which does not have an expression vector encoding the selectable marker. An example is a host cell which can use the selectable marker to survive a selection process that would otherwise kill the host cell, such as treatment with an antibiotic. Such a selective marker can be antibiotic resistance factors, such as neomycin resistance (e.g. neo), hygromycin resistance, puromycin resistance. A selectable marker can also be a cell surface marker, such nerve growth factor receptor or cytoplasmicly truncated versions thereof. Cells are expressing the cell surface marker can then be selected using an antibody targeted to the cell surface maker. The antibody targeted to the cell surface marker can be directly labeled (e.g., with a fluorescent substrate) or can be detected using a secondary labeled antibody or substrate which binds to the antibody targeted to the cell surface marker. Alternatively, cells can be negatively selected for using an enzyme, such as herpes simplex virus thymidine kinase (HSVTK) that converts a pro-toxin (gancyclovir) into a toxin. Alternatively, any nucleic acid sequence encoding a polypeptide can be used as a selectable marker as long as the polypeptide is easily recognized by an antibody.

The nucleic acid encoding a selectable marker can encode, for example, a beta-lactamase, a luciferase, a green fluorescent protein (GFP), beta-galactosidase, or other reporter gene as that term is understood in the art, including cell surface markers, such as CD4 or the truncated nerve growth factor (NGFR) (for GFP, see WO 96/23810 to Tsien, published Aug. 8, 1996; Heim et al., Current Biology, 2:178–182 (1996), Heim et al., Proc. Natl. Acad. Sci. U.S.A (1995), or Heim et al., Science 373:663–664 (1995); for beta-lactamase, see WO 96/30540 to Tsien published Nov. 3, 1996). In a preferred embodiment, the selectable marker is a beta-lactamase. The nucleic acid encoding a selectable marker can encode, for example, a fluorescent protein. A fluorescent protein can be detected by determining the amount of any quantitative fluorescent property, e.g., the amount of fluorescence at a particular wavelength, or the integral of fluorescence over an emission spectrum. Optimally, the fluorescent protein is selected to have fluorescent properties that are easily detected. Techniques for measuring fluorescence are well known to one of skill in the art.

The non-optimal translational initiation start site of the present invention may be included in a vector. A "vector" is any nucleic acid capable of transferring genetic material into a host organism. The vector may be linear or circular in topology and may include a restriction endonuclease site, which can be in close proximity to the non-optimal translational initiation start site. "In close proximity" indicates that the restriction endonuclease site is near to the non-optimal translational initiation start site, and can be within 0 to 200 base pairs of the non-optimal translational initiation start site.

The non-optimal translational start site can be used as part of a methionine start codon that initiates the translation of a selectable marker of a transcriptional cassette that is part of an expression vector. "Operatively linked" refers to a juxtaposition wherein the components so described are in a relationship permitting them to function in their intended manner. For example, a DNA sequence encoding a polypeptide and a regulatory sequence(s) are operatively linked if they are connected in such a way as to permit gene expression when the appropriate molecules (e.g., transcriptional activator proteins) are bound to the regulatory sequence(s). By "operatively inserted" is meant that the nucleic acid sequence of interest is positioned adjacent a nucleic acid sequence that directs transcription or translation of the introduced nucleic acid. For example, the nucleic acid sequence can facilitate the production of, e.g., a polypeptide encoded by a nucleic acid sequence of interest.

Nucleic acid sequences including the translational start site of the invention can be utilized in vitro by nucleic acid transfer into a suitable host cell. By "transformation" is meant a genetic change induced in a host cell following incorporation of new nucleic acid (for example, DNA exogenous to the cell). The new DNA can be present in the host cell as an extrachromosomal or chromosomally integrated element. Where the host cell is a mammalian cell, the genetic change is generally achieved by introduction of the DNA into the genome of the cell (for example, stable). Methods of stable transfer, meaning that the new nucleic acid is preferentially maintained in the host, such as integrating the new nucleic acid into the genome of the host, are known in the art. A "target cell" is a cell that is to be transformed. Transformation may be designed to nonselectively or selectively transform the target cell. "Host cells" are cells in which a vector can be propagated and its nucleic acid expressed, and include prokaryotic or eukaryotic cells. The non-optimal translational start site of the invention can be utilized in either prokaryotic cells or eukaryotic cells, such as, for example, bacterial, yeast, insect, and mammalian cells. The term also includes any progeny of the subject host cell. It is understood that all progeny may not be identical to the parental cell since there may be mutations that occur during replication. However, such progeny are included when the term "host cell" is used.

A "transformed cell" is a host cell into which (or into an ancestor of which) has been introduced, by means of recombinant DNA techniques, a nucleic acid including the non-optimal translational start site of the invention. Transformation of a host cell with recombinant DNA may be carried out by conventional techniques as are well known to those skilled in the art. Where the host cell is a prokaryotic cell, such as E. Coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host cell is a eukaryotic cell, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with nucleic acid sequences utilizing the non-optimal translational start site of the invention and a selectable marker, and a second distinct foreign nucleic acid molecule encoding a second selectable marker. Another method is to use a eukaryotic viral vector, such as a retrovirus, adenovirus, adenovirus associated virus, simian virus 40 (SV40) or bovine papilloma virus, to transiently infect or transform eukaryotic cells and then utilize the translational start site of the invention to express a selectable marker (see for example, Eukaryotic Viral Vectors, Cold Spring Harbor Laboratory, Gluzman ed., 1982, and PCT/US97/17395 to Whitney et al., filed Sep. 25, 1997).

In the present invention, the polynucleotide sequences encoding the non-optimal translational start site of the invention can be inserted into a vector. DNA fragments, without a plasmid or viral vector, can also be used. By "vector" is meant any compound or formulation, biological or chemical, that facilitates transformation or transfection of a target cell with a nucleic acid sequence of interest. Exemplary biological vectors include plasmids, linear nucleic acid molecules, and viruses, preferably attenuated and/or replication-deficient viruses. Exemplary chemical vectors include lipid complexes and DNA constructs. Methods of expressing nucleic acid sequences having eukaryotic or viral sequences in prokaryotes are well known in the art. Biologically functional viral and plasmid nucleic acid vectors capable of expression and replication in a host are known in the art. Such vectors are used to incorporate nucleic acid sequences of the invention into host cells. The vector can be an expression vector.

The term "expression vector" refers to a plasmid, virus or other vehicle known in the art that has been manipulated by insertion or incorporation of genetic sequences encoding the translational start site of the invention. Expression control sequences can be incorporated into the expression vector. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. A "stop codon" is a codon that does not encode an amino acid such that translation of the encoded material can be terminated. This includes, but is not limited to, the traditional stop codons TAA, TAG, and TGA. The terms "in-frame" and out-of-frame" are relative to the non-optimal Kozak sequence. The term "expression control sequences" is intended to included, at a minimum, components whose presence can influence expression, and can also include additional components whose presence is advantageous, for example, leader sequences and fusion partner sequences. Expression control sequences can include a promoter.

By "promoter" is meant a DNA sequence sufficient to direct transcription of a DNA sequence to which it is operably linked. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., 1987, Methods in Enzymology 153:516–544). For example, when cloning in bacterial systems, inducible promoters such as pL of bacteriophage γ, plac, ptrp, ptac (ptrp-lac hybrid promoter) and the like can be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences of the invention.

In the present invention, the polynucleotide including a non-optimal translational start site of the invention can be inserted into an expression vector which contains a promoter sequence which facilitates the efficient transcription of the inserted genetic sequence of the host. The expression vector typically contains an origin of replication, a promoter, and at least one gene that allows phenotypic selection of the transformed cells. Vectors suitable for use in the present invention include, but are not limited to the T7-based expression vector for expression in bacteria (Rosenberg el al., 1987, Gene, 56:125), the pMSXND expression vector for expression in mammalian cells (Lee and Nathans, 1988, J. Biol. Chem., 263:3521) and baculovirus-derived vectors for expression in insect cells. A selectable marker can be present in the vector operably linked to regulatory elements, for example, a promoter (e.g., T7, metallothionein I, or polyhedrin promoters).

Retroviral vectors can also be utilized with a non-optimal translational start site of the invention, and can be made using methods known in the art (see Sambrook et al., Molecular Cloning: a Laboratory Manual (Cold Spring Harbor Press 1989), the contents of which are incorporated by reference). For example, the non-optimal translational start site of the invention can be positioned between the long terminal repeats (LTRs) of a retroviral vector. Alternatively, the non-optimal translational start site of the invention can be positioned within a LTR of a retroviral vector. Plasmids encoding elements of a retrovirus can be made using standard recombinant DNA methods. These plasmids are introduced into retroviral packaging cell lines, such as PT67, using standard gene transfer techniques, such as electroporation, calcium phosphate transfection, and lipofection. Packaging cell lines with integrated plasmid constructs, known as retroviral producer cells, can be selected by antibiotic resistance or cell sorting for a reporter gene, when appropriate. Ping-pong techniques can be used to increase the titer of the retroviral vectors (Kozak and Kabat, J. Virol. 64:3500–3508 (1990)). Identification of high titer producer cell clones can be accomplished using RNA dot blot hybridization, antibiotic resistance, or reporter gene expression. Titers of retrovirus preparations can be increased by culturing retroviral producer cells at 32° C. rather than 37° C., selecting for packaging cell functions, and concentrating methods such as centrifugation to pellet retroviruses and by lyophilization. Also, transduction efficiency of retroviruses can be increased by centrifugation methods as are known in the art and by performing transductions at 32° C. rather than 37° C. Virus titers can also be increased by co-cultivating producer cells with target cells and be incubating target cells in phosphate-free media prior to infection.

Other examples of viral vectors that can be utilized with the subject invention are the pSIR vector (available from ClonTech of California with PT67 packaging cells). GgU3Hisen and GgTNKneoU3 and GgTKNeoen variants of Moloney murine leukemia virus are also of use with the subject invention. Vector modifications can be made that allow more efficient integration into the host cell genome. Such modifications include sequences that enhance integration or known methods to promote nucleic acid transportation into the nucleus of the host cell. Retroviral vectors, such as those described in U.S. Pat. No. 5,364,783 to Ruley and von Melchner can also be used (see WO 98/13353, Whitney et al., published Apr. 2, 1998). Additional retroviral vectors of the present invention include double copy retroviral vectors. Vectors of use with the present invention can also be adeno-associated viruses (AAVs). (See WO 98/13353 to Whitney et al., published Apr. 2, 1998).

Vectors can also be used with liposomes or other vesicles that can transport genetic material into a cell. Appropriate structures are known in the art. The liposomes can include vectors such as plasmids or yeast artificial chromosomes (YACs), which can include genetic material to be introduced into the cell.

The non-optimal translational start site of the present invention can be used to translate any nucleic acid sequence of interest in a host cell. One use of the non-optimal translational start site of the invention is in identifying cellular genes and their expression control sequences. Nucleic acid encoding a non-optimal translational start site of the invention is operatively linked to a selectable marker and introduced into a host cell. The nucleic acid encoding a non-optimal translational start site of the invention operatively linked to a selectable marker is integrated within the cellular DNA of a host cell. Without being bound by theory, the position where the nucleic acid encoding a non-optimal translational start site of the invention operatively linked to a selectable marker is integrated within the cellular DNA of a host cell then can determine the level of expression of the gene of interest. The expression of a cellular gene which is either co-linked to or positioned near the gene of interest can be proportional to the expression of the gene of interest. If the gene used to select for the integration of the exogenous DNA in the mammalian cell (i.e. a selectable marker) is designed such that translation of that selectable marker is impaired, then only those sequences that could overcome such impairment by allowing over-production of the selectable marker can be identified. Thus, impairment of the translation of the selectable marker by the non-optimal translational start site of the invention is preferable so that the appropriate cellular gene sequences are identified.

The above disclosure generally describes the present invention. A more complete understanding can be obtained by reference to the following specific examples which are provided herein for purposes of illustration only and are not intended to limit the scope of the invention.

EXAMPLE 1

BETA-LACTAMASE EXPRESSION CONSTRUCTS

Figure 1A:
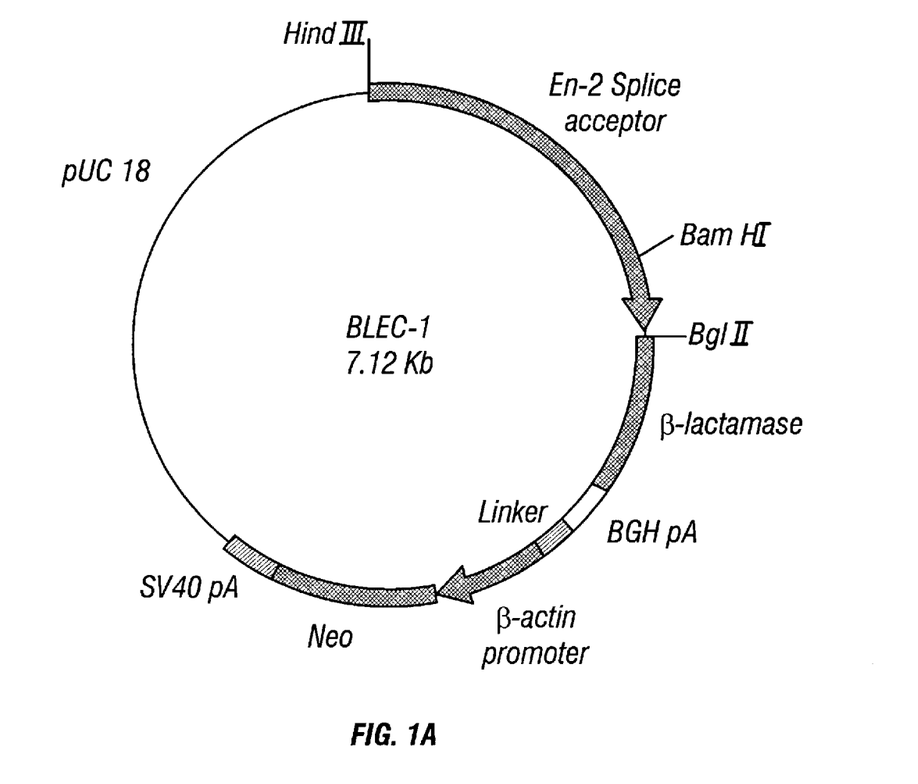
FIG. 1A and 1B shows a schematic plasmid map of BLEC-1 and a viral vector map of BLEC-RV1, respectively.
Figure 1B:
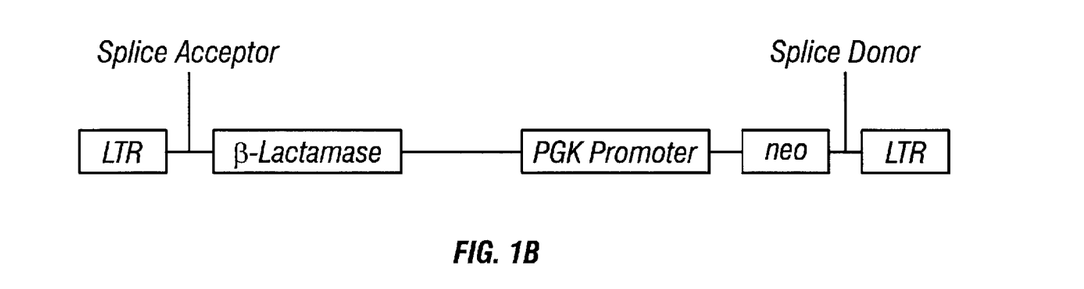

To investigate the use of the non-optimal Kozak's sequence of the present invention, the beta-lactamase expression constructs (BLEC-1) was constructed and transfected into mammalian cells. BLEC-1 was constructed by cloning the cytoplasmic form of BL (see WO 96/30540, published Nov. 3, 1996; and WO 98/13353, published Apr. 2, 1998) such that it was functionally linked to a non-optimal Kozak's sequence (SEQ ID NO: 2) such that the expression of the cytoplasmic form of BL was driven by the non-optimal Kozak's sequence. No additional nucleotides were present at the junction of the cytoplasmic form of BL and SEQ ID NO: 2. Furthermore, the En-2 splice acceptor sequence, was engineered upstream of the non-optimal Kozak's sequence and gene encoding the cytoplasmic form of BL (FIG. 1). This vector, when inserted into a genomic intron will result in the generation of a fusion RNA between an endogenous target gene and BL. BLEC-1 also contains a bovine growth hormone poly-adenylation sequence (BGH-polyA) downstream of the cytoplasmic Beta-lactamase (Table 1). The structure of CCF2-AM (BL substrate) used in the experiments below is:

suggests that the BLEC-1 construct is functioning as a gene integration vector.

Stable cell lines were also generated by transfecting BLEC-1 into CHO-K1 and Jurkat cells. Populations of BLEC-1 integrated clones from CHO and Jurkat cells showed similar results to those obtained with RBL-1 clones with 10–15% of BLEC integrated cell clones expressing BL as determined by their blue/green ratio after loading with CCF-2-AM. This result shows that BLEC-1 functions in a variety of cell types including human T-cells (Jurkat), rat basophilic leukocytes (RBL), and Chinese hamster ovarian (CHO).

CCF2-AM

TABLE 1

Functional Elements

| | Splice acceptor | Adapter | Re-porter gene | Re-porter gene poly A | Selection Promoter | Resistant Marker poly A |
|---|---|---|---|---|---|---|
| VECTOR BLEC-1 | En2-splice acceptor | Non-optimal Kozak's (SEQ ID NO: 2) | | BGH poly A | β-actin promoter | Neo poly A |

EXAMPLE 2

LIBRARIES OF BLEC-1 CLONES

To investigate the function of the BLEC-1 vector, it was transfected by electroporation into RBL-1 cells and stable clones were selected. Selective media contained DMEM, 10% fetal bovine serum (FBS) and 400 μg/ml Geneticin (G418). G418 resistant cell clones were pooled from multiple transfections to generate a library of BLEC-1 stable integrated clones.

This library of BLEC-1 integrated clones was loaded with the fluorescent substrate of BL (CCF-2-AM) by adding 10 mM CCF-2-AM in HBSS containing 10 mM hepes 7.1 and 1% glucose. After a 10 hour incubation at 22° C. cells were washed with HBSS and viewed upon excitation with 400 nm light using a 435 nm long pass emission filter. Under these assay conditions 10% of the cells were blue fluorescent indicating they were expressing beta-lactamase. This result

EXAMPLE 3

ISOLATING BLEC-1 CLONES EXPRESSING BETA-LACTAMASE

Figure 2A:
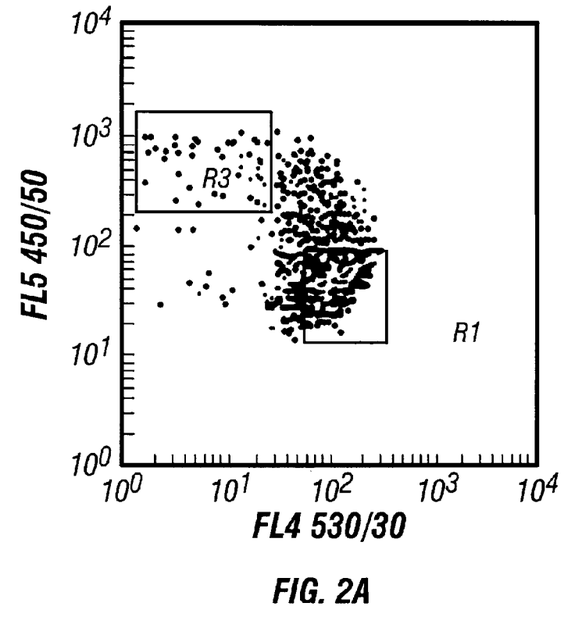
FIG. 2A shows an unselected muticlonal population of BLEC integrated RBL-1 clones.
Figure 2B:
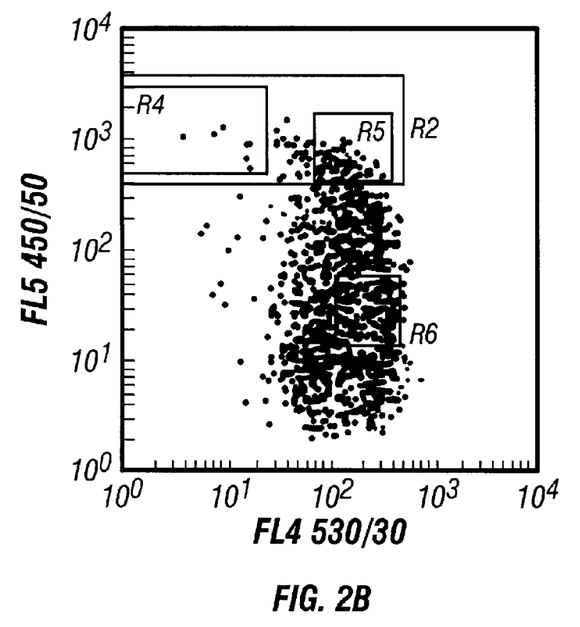
FIG. 2B show the population of clones from FIG. 1A(R1) that were cultured for an additional seven days and resorted.

Fluorescent activated cell sorting of multi-clonal populations of RBL-1 gene integrated clones was used to identify clones with regulated BL gene expression. A BL non-expressing population of cells was isolated by sorting a library of BLEC-1 integrated clones generated by transfection of RBL-1 cells as described in Example 2. 180,000 clones expressing little or no BL were isolated by sorting for clones with a low blue/green ratio (R1 population), as shown in FIG. 2A. This population of clones was grown for seven days and resorted by FACS to test the population's fluorescent properties. FACS analysis of the cell clones sorted from R1 shows that most of the cells with a high blue/green ratio ~0.1% have been removed by one round of sorting for green cells, as shown in FIG. 2B. It is also clear that the total population has shifted towards more green cells compared to the parent population, as shown in FIG. 2A. There are, however, cells with a high blue/green ratio showing up in the green sorted population. These may represent clones in which the BLEC-1 has integrated into a differentially regulated gene such as a gene whose expression changes throughout the cell cycle.

The population of RBL-1 clones shown in FIG. 2B was stimulated by addition of 1 μM ionomycin for 6 hours and resorted to identify clones which had the BLEC-1 integrated into a gene which is inducible by increasing intracellular calcium. Table 2 below summarizes the results from this experiment. A greater percentage of blue clones were present in all three of the blue sub-population (R4, R2, R5) in the ionomycin stimulated when compared to the unstimulated population. This sorted population represents the following classes of blue cells: R4 (highest blue/green ratio (bright blues)), R2 (multicolor blues), and R5 (lower blue/green ratio (least blue). Additionally, in the ionomycin stimulated population there is a decrease in the percent green cells from the unstimulated population (R6). This increase in blue clones in the ionomycin stimulated population indicates that a sub-population of blue clones have the BLEC-1 inserted into a gene which is induced by ionomycin. Individual blue clones were sorted from the ionomycin stimulated population and are analyzed for their expression profile.

TABLE 2

Figure 2C:
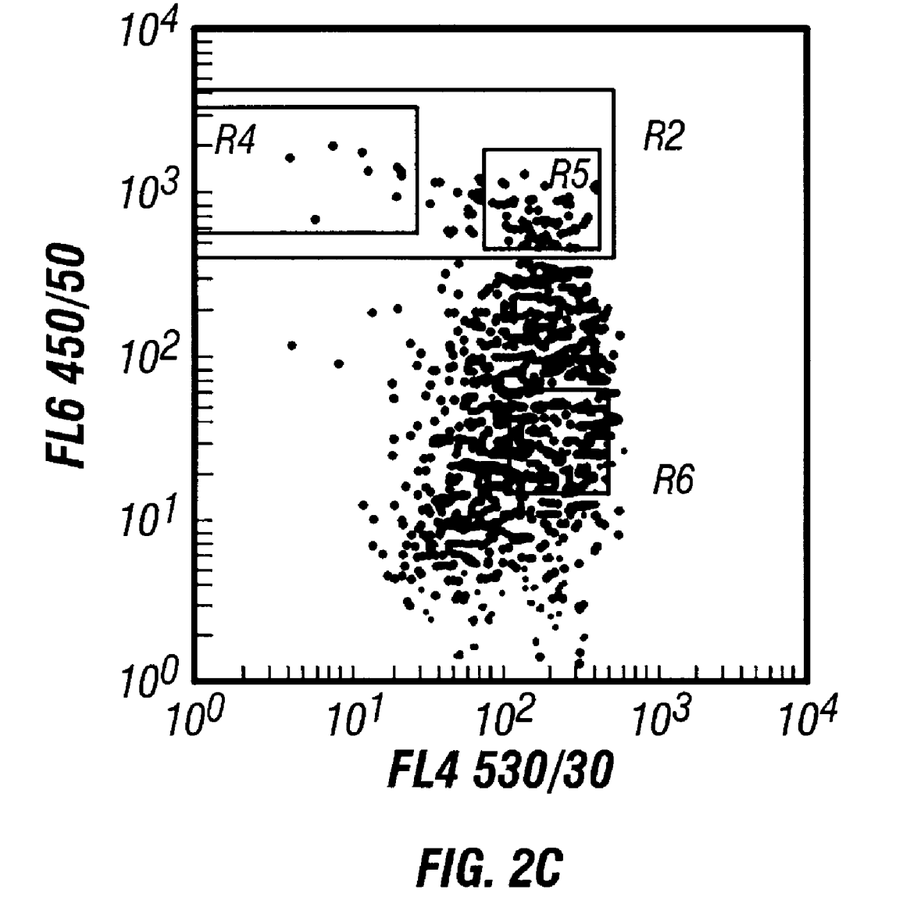
FIG. 2C shows the population from 1B with addition of 1 $\mu$M ionomycin for 12 hours prior to sorting.

| | Sort Window (See FIG. 2) | | | |
|---|---|---|---|---|
| | R4 (blue) | R2 | R5 | R6 (green) |
| Unstimulated % | .11 | 2.39 | 1.53 | 66.23 |
| 1 uM Ionomycin Stimulated % | .24 | 3.5 | 2.5 | 61.64 |
| Ratio + Ion/−Ion | 2.2 | 1.5 | 1.6 | .9 |

In addition to allowing the isolation of cell clones with inducible BL expression from large populations of cells, clones can be isolated based their level of BL expression. To isolate cells with different levels of BL expressions blue clones can be sorted after different exposure times to substrate or by their blue/green ratio. Cell with a lower blue/green ratio or those requiring longer incubation times will represent clones expressing lower levels of BL. This is demonstrated by the FACS scan above as clones sorted from the R4 window have a higher blue/green ration indicating they are expressing higher levels of BL, cells sorted from the R5 have a lower blue/green ratio (visually turquoise) indicating lower BL expression. Cell sorted from the R3 window which contain all the blue cells show variation in blue color from bright blue (high blue/green ratio) to turquoise blue (low blue/green ratio).

To demonstrate that the expression constructs are relatively stable for sorted clones cells were sorted from R3 (blue population) as shown in FIG. 2A and cultured in the absence of selective pressure for several weeks. There was little change in the percent of blue cells in the cultured population with the percent blue being maintained at ~90%. This result represents a 10-fold enrichment for clones constitutively expressing BL by one round of FACS selection. Cells in R6 window have the lowest blue/green ration and appear green visually. R6 cell is therefore not expressing BL or are expressing Bl below the detection limit of our assay.

EXAMPLE 4

STABILITY OF BLEC-1 CLONES

To further investigate the stability of reporter gene integrations into constitutively active genes, single blue clones were sorted from cell clone populations generated by transfecting RBL-1, and CHOK1 with BLEC-1. After addition of CCF-2 to the multi-clonal cell population, single blue clones were sorted into 96 well microtiter plates. These clones were expanded to 24 well dishes, which took 7–10 days. The cell viability varied between the two cell types with 80% of the sorted clones forming colonies for the CHO and 36% for the RBL-1 cells. After expansion into a 24 well dishes 20 CHO BLEC-1 stable clones were tested for BL expression by addition of CCF-2-AM. 20/20 of these clones expressed BL with the percent blue cells within a clone ranging from 70% to 99%. This result is consisted with the earlier data presented for RBL-1 in which the blue sorted population was tested for BL expression after several weeks of non-selective culturing. There was however a significant differences between clones in their blue/green ratio and hence their level of BL expression. This suggested that genes with different levels of constitutive expression had been tagged with the BLEC-1. Although there was a significant differences in blue color between separate clones the blue fluorescence within a clone was consistently similar as would be expected in a clonal population. There were however green cells within the blue sorted clones, which may indicate that there is some loss of the BLEC-1 plasmid integration site when clones are grown up from a single cell.

Single clones were expanded and used to make RNA for RACE to identify the target gene and DNA for southern analysis.

EXAMPLE 5

ISOLATION OF JURKAT BLEC INTEGRATED CLONES THAT CONSTITUTIVELY EXPRESS BETA-LACTAMASE

Jurkat cells are a T-cell line derived from a human T-cell leukemia. This cell line maintains many of the signaling capabilities of primary T-cells and can be activated using anti-CD3 antibodies or mitogenic lectins such as phytohemaglutinin (PHA). Wild type Jurkat cells were transfected by electroporation with a beta-lactamase trapping construct (BLEC-1) ("BLEC constructs") that contains a gene encoding an beta-lactamase gene that is not under control of a promoter recognized by the Jurkat cells and a neomycin resistance gene that can be expressed in Jurkat cells. BLEC-1 is set forth in FIG. 1 (see WO98/13353 Whitney et al., published Apr. 2, 1998, herein incorporated by reference). This allows the cutting of the insert away form the plasmid backbone. Stable transformants were selected for their resistance to 800 µg/ml G418. After 400 separate experiments, a pool of greater than one million clones with BLEC insertions was produced. This population of cells is a library of cell clones in which the BLEC construct inserted throughout the genome ("Jurkat BLEC library"). Approximately ten percent of the cells in this library express beta-lactamase in the absence of added stimuli. Beta-lactamase activity in the cells was determined by contacting the cells with CCF2-AM. Individual clones or populations of cells that express beta-lactamase can be obtained by FACS sorting.

Genomic Southern analysis of these clones using a DNA probe encoding beta-lactamase showed the vector inserted into the host genome between one and three times per cell, with most clones having one or two vector insertion sites (for Genomic Southern analyses, see Sambrook, Molecular Cloning, A Laboratory Manual, Cold Spring Harbor Laboratory Press (1989)). Northern analysis of these clones using a DNA probe that encodes beta-lactamase showed that the level of expression and message size varied from clone to clone (for Northern analysis, see Sambrook, supra, (1989)). This indicated that fusion transcripts were being made with different genes functionally tagged with beta-lactamase, which allows for the reporter gene to be expressed under the same conditions as the endogenous gene. Using appropriate primers, RACE (Gibco BRL) was used to isolate the genes linked to the expressed beta-lactamase gene in a subset of these constitutively expressing clones. These genes were cloned and sequenced using known methods (see, Sambrook, supra, (1989)). These sequences were compared with known sequences using established BLAST search techniques. Known sequences that were identified included: beta-catenin, moesin, and -adaptin. Additionally, several novel sequences were identified which represent putative genes.

EXAMPLE 6

ISOLATION OF JURKAT BLEC-1 INTEGRATED CLONES THAT SHOW INDUCED EXPRESSION OF BETA-LACTAMASE UPON ACTIVATION

Jurkat BLEC-1 integrated clones that exhibit beta-lactamase expression upon activation of the Jurkat cells by PHA (PHA induced clones) were isolated by FACS sorting a Jurkat BLEC-1 library. These clones represent cells in which the trapping construct had integrated into a gene up regulated by PHA (T-cell) activation. Thus, these cells report the transcriptional activation of a gene upon cellular activation. Individual clones were identified and isolated by FACS using CCF2-AM to detect beta-lactamase activity. This clone isolation method, the induced sorting paradigm, used three sequential and independent stimulation and sorting protocols. A FACS read out for Jurkat cells that don't contain a BLEC-1 construct contacted with CCF2-AM was used as a control. These control cells were all green.

The first sorting procedure isolated a pool of blue (beta-lactamase expressing, as indicated by contacting the cells with CCF2-AM) clones which had been pre-stimulated for 18 hours with 10 $\mu$g/ml PHA from an unsorted Jurkat BLEC-1 library. This pool represented 2.83% of the original unsorted cell population. This selected pool contained clones that constitutively express beta-lactamase and clones in which the beta-lactamase expression was induced by PHA stimulation ("stimulatable clones"). After sorting, this pool of clones was cultured in the absence of PHA to allow the cells, in the case of stimulatable clones, to expand and return to a resting state (i.e. lacking PHA induced gene expression).

The second sorting procedure isolated a pool of green (non-beta-lactamase expressing, as indicated by contacting the cells with CCF2-AM) cell clones from the first sorted pool that had been grown, post-sorting, without PHA stimulation for 7 days. The second sorting procedure separates clones that constitutively express beta-lactamase from cells that express beta-lactamase upon stimulation. This second pool represented 11.59% of the population of cells prior to the second sort. This pool of cells was cultured in the absence of PHA to amplify the cell number prior to a third sort.

The third sorting procedure used the same procedure as the first sorting procedure and was used to isolate individual cells that express beta-lactamase in response to being contacted with 10 $\mu$g/ml PHA for 18 hours. Single blue clones were sorted individually into single wells of 96 well microtiter plates. This three round FACS sorting procedure enriched PHA inducible clones about 10,030 fold.

These isolated clones were expanded and tested for PHA inducibility by microscopic inspection with and without PHA stimulation in the presence of CCF2-AM. A total of fifty-five PHA inducible clones were identified using this procedure. The PHA inducibility for these clones ranged from a 1.5 to 40 fold change in the 460/530 ratio as compared to unstimulated control cells. Genomic Southern analysis using a DNA probe encoding beta-lactamase established that these clones represented 34 independent stable vector integration events. A list of clones obtained by the methods of the present invention and their characteristics is provided below in Table 4 and Table 5.

In addition to Phobol inducible clones, Phobol 12-myristate 13-acetate (PMA) (Calbiochem), Thapsigargin (Thaps) (Calbiochem), and PMA+Thaps inducible clones were isolated using the general procedure set forth above using the indicated inducer rather than PHA. PMA is a specific activator of PKC (protein kinase C) and Thaps is a specific activator of intracellular calcium ion release (Thaps). These clones were isolated using three rounds of FACS using the general procedures described for the PHA inducible clones in Example 5. In such instances, other stimulants were substituted for PHA. PMA was provided at 8 nM, Thaps was provided at 1 $\mu$M. When these two stimulants were combined, their concentration was not changed. As shown in Table 3, clones were selected based on their activation by PMA, Thaps, or PMA with Thaps after three or eighteen hours of stimulation ("stimulation time"). These results demonstrate that the FACS sorting criteria can be varied depending upon the type of modulated clones desired. By using varied selection conditions, it is possible to isolate functionally distinct clones downstream of the desired signaling target.

EXAMPLE 7

ISOLATION OF JURKAT BLEC-1 INTEGRATED CLONES THAT SHOW REPRESSED EXPRESSION OF BETA-LACTAMASE UPON ACTIVATION

Jurkat BLEC clones that exhibit decreased beta-lactamase expression upon activation of the Jurkat cells by PHA were isolated by FACS sorting. These clones represent cells in which the BLEC-1 trapping construct had integrated into a gene down regulated by PHA (T-cell) activation. Thus, these cells report the transcriptional repression of a gene upon cellular activation. Individual clones were identified and isolated by FACS using CCF2-AM to detect beta-lactamase activity using the following repressed sorting paradigm.

A first sort was used to isolate a population of cells that constitutively express beta-lactamase by identifying and isolating a population of blue cells from an unstimulated population of BLEC-1 transfected Jurkat cells contacted with CCF2-AM. The sorted population of cells represented 2.89% of the unsorted population. These cells were cultured, divided into two pools, and stimulated with one of two different stimuli, either 10 $\mu$g/ml PHA for 18 hours, or 8 nM PMA and $\mu$M Thapsigargin for 18 hours. These stimulated cells were contacted with CCF2 and the green cells in the population were sorted using FACS. The sorted population represented 8.41% of the cell population prior to the second sort. The third round of FACS was for single blue unstimulated cells. The population of cells obtained represented 18.2% of the cell population prior to the third sort.

This sorting procedure represents a 2,260-fold enrichment for PHA repressible clones. These clones have the beta-lactamase gene integrated into a gene that is down regulated by PHA stimulation of the cells. Six of 80 individual clones tested were repressed by PHA or PMA+Thapsigargin. All of these clones were confirmed to be independent integration events by genomic Southern analysis using a DNA probe encoding beta-lactamase. The results of these studies are presented in Table 3.

TABLE 3

Identification of trapping cell lines with reporter genes expression which is regulated by T-cell activation

| Stimuli (Dose) | First Sort Activation Chemical and Time of Exposure | Stimulation Time | Sorting Paradigm | Clones Isolated | Clones with One or Two Vector Insertion(s) 1 | 2 |
|---|---|---|---|---|---|---|
| PHA (10 μg/ml) | PHA 18 hours | 18 hours | Induced | 34 | 24 | 10 |
| PMA (8 nM/Ml) + (Thaps (1 μM) | PMA + Thaps 3 hours | 3 hours | Induced | 2 | 2 | 0 |
| PMA (8 nM/ml) | PMA 3 hours | 3 hours | Induced | 3 | 2 | 1 |
| Thaps (1 μM) | Thaps 3 hours | 3 hours | Induced | 2 | 2 | 0 |
| PHA (10 μg/ml) or PMA (5 ng/ml + Thaps (1 μM) | No Stimulation | 18 hours | Repressed | 6 | 5 | 1 |

EXAMPLE 8

SPECIFICITY OF T-CELL MODULATED CLONES

Isolated clones from PHA-induced (Example 6) and PHA-repressed (Example 7) procedures described above were characterized to determine the specificity of their modulation and time required for induction or repression. Clones were stimulated with multiple activators or inhibitors over a one to twenty-four hour time interval. As shown in Table 4, five clones produced by the induced and repressed sorting paradigms using a plurality of activators were tested for their responsiveness to a variety of T-cell activators, suppressors, and combinations thereof.

TABLE 4

Sorting protocols and specificity of activated BLEC-1 Jurkat clones

| | | Sorting Procedures | | | Relative Beta-Lactamase Activity of the Clone by the Indicated Stimulus After 24 hours (% of maximum activated stimuli) | | | | | |
|---|---|---|---|---|---|---|---|---|---|---|
| Clone | Paradigm | First Sort Stimulus and (cell color sorted for) | Second Sort Stimulus and (cell color sorted for) | Third Sort Stimulus And (cell color sorted for) | None | PMA (8 nM) | Thaps (1 μM) | PMA (8 nM) + Thaps (1 μM) | PMA (8 nM) + Thaps (1 μM) + CsA (100 nM) | PHA (10 μM) | PHA (8 nM) + CsA (100 nM) |
| J83-P19 | Induced | PHA[a] (blue) | N/S (green) | PHA (blue) | 0 | <1 | 100 | 50 | <5 | 60 | <5 |
| J32-6D4 | Induced | PHA (blue) | N/S (green) | PHA (blue) | 0 | 60 | 1–2 | 100 | 70 | 80 | 75 |
| C2 | N/S | N/S | N/S | N/S | 0 | <1 | 0 | 100 | <1 | 30 | 1 |
| J389-PT14 | Induced | PMA[b] + Thaps[c] (blue) | N/S (green) | PMA+ Thaps (blue) | 0 | 90 | 5 | 85 | 100 | 85 | 90 |
| J8397-PPTR2 | Repressed | PMA + Thaps (green) | PHA or PMA + Thap (green) | N/S (blue) | 0 | 100 | 85 | −50 | 85 | 67 | 75 |
| J83-PT18 | Induced | PHA (blue) | N/S (green) | PHA (blue) | 0 | 80 | 100 | 25 | 70 | 60 | 60 |

"N/S" means "no stimulation"
[a]concentration of PHA used was 10 μg/ml.
[b]concentration of PMA used was 8 nM.
[c]concentration of Thaps used was 1 μM.

In this study, PMA, which is a PKC activator, Thapsigargin which increases intracellular calcium, PHA which activates the T-cell receptor pathway, and cyclosporin A which is a clinically approved immunosuppressant that inhibits the Ca2+ dependent phosphates calcineurin were investigated for their ability to modulate beta-lactamase expression in PHA induced and repressed BLEC-1 clones.

The selected clones show varied dependence for their activation and inhibition by these activators and inhibitors which give and indication of the signaling events required for their transcriptional activation. Five of the listed clones were generated using the approaches described above in Example 6. The clone C2 was generated using a more classical approach. This clone was generated by transfecting a plasmid construct in which a 3XNFAT response element has been operably linked to beta-lactamase expression. This 3XNFAT element represents a DNA sequence that is present in the promoter region of IL-2 and other T-cell activated genes. In addition the C2 cell line has been stably transfected with the M1 muscurinic receptor. This allows the activation of beta-lactamase expression in this clone using an M1-muscurinic agonist such as carbachol. This cell line therefore represents a good control for the cellular activators and inhibitors tested as the signaling events required for its activation are established.

The results of these studies indicate that the cell lines generated vary in their specificity towards activation or repression by activators. Thus, depending on the type of system that these cells are to be used to investigate, a pool of cells with varying specificity towards a specific pathway are made available by the present methods.

Table 5 provides data similar to that provided in Table 3 for the clones obtained by the methods of Examples 5 to 7.

To confirm that changes in reporter gene activity reflected changes in mRNA expression in these clones, Northern analysis was performed on induced, constitutive, and repressed clones using a radiolabeled DNA probe directed towards the beta-lactamase gene. All clones that had beta-lactamase enzyme inducibility tested showed beta-lactamase mRNA inducibility. All clones that showed constitutive expression of beta-lactamase showed constitutive expression of beta-lactamase mRNA. All clones that showed repressed beta-lactamase expression showed repressed beta-lactamase mRNA. The message size of the control beta-lactamase mRNA was about 800 base pairs. The sizes of some of the RNA were shifted higher in the gel, indicating the a fusion RNA had been made between the endogenous transcript and the beta-lactamase gene. Two known genes, CDK-6 (isolated from clone J83-PTI1) and Erg-3 (isolated from clone J89-PTI4), and two unknown genes were identified, which were isolated from clones J83PI 15 and J83PI2, respectively. For clone J389-PTI4, a Northern blot was performed with the Erg-3 probe made using appropriate PCR primers determined from a published sequence which hybridizes with both the fusion RNA and the wild type RNA (for the sequence of Erg-3 see Stamminger et al., Int. Immunol. 5:63–70 (1993); for PCR methodologies, see U.S. Pat. Nos. 4,800,159, 4,683,195, and 4,683,202). The inducibility in wild type Jurkat cells mimicked the beta-lactamase activity in this clone.

Although the invention has been described with reference to the presently preferred embodiments, it should be under-

TABLE 5

Characterization of induced BLEC-1 Jurkat clones

| CLONE Number | TIME (hours) for first detectable change in color | Change in 450/530 ratio in the indicated clone by the following activator | | | | |
|---|---|---|---|---|---|---|
| | | PHA (10 μg/ml) | Thaps (1 μM) | PMA (8 nM) | PMA (8 nM) + Thaps (1 μM) | Anti-CD3 (2 μg/ml) (Pharmigen) |
| J325B5 | 6 | 7 | Nt | 2–3 | Nt | 4–5 |
| J325B11 | 6 | 9 | 1–2 | 2–3 | Nt | 5–6 |
| J325E3 | 6 | 7 | Nt | 2–3 | Nt | 4–5 |
| J325G4 | 6 | 3–4 | Nt | 3–4 | Nt | 4–5 |
| J325E6 | 6 | 11 | Nt | 3–4 | Nt | 6 |
| J326C9 | 6 | 4–5 | 1–2 | 2–3 | Nt | 3–4 |
| J325E1 | <2 | 8 | Nt | 8 | Nt | 5–6 |
| J326D4 | <2 | 10 | 0 | 10 | Nt | 5–6 |
| J326D7 | <2 | 10 | Nt | 10 | Nt | 5–6 |
| J326F7 | <2 | 10 | Nt | 10 | Nt | 5–6 |
| J326H4 | <2 | 10 | Nt | 10 | Nt | 5–6 |
| J83PI1 | NT | 3–4 | 3–4 | 3–4 | 4–5 | 2–3 |
| J83PI2 | 5–6 | 8 | 1–2 | 7–8 | 7–8 | 3–4 |
| J83PI8 | 5–6 | 4–5 | 1–2 | 4–5 | 4–5 | 2–3 |
| J83PI3 | 5–6 | 5–6 | 6–7 | 3–4 | 5–6 | 2–3 |
| J83PI4 | 4–6 | 3–4 | 3–4 | 0 | 2–3 | 2 |
| J83PI6 | 6–18 | 6–7 | 7–8 | 0 | 4–5 | 4 |
| J83PI9 | 6 | 6 | 5–6 | 0 | 4–5 | 3–4 |
| J83PI5 | Nt | Nt | Nt | Nt | Nt | Nt |
| J83PI7 | 6–18 | 2 | 2 | 2 | 2 | 1.5–2 |
| J83PI15 | Nt | 3–4 | 2 | 3–4 | 3–4 | 3–4 |
| J83PI16 | Nt | 3–4 | 1–2 | 3–4 | 3–4 | 2–3 |
| J83PI18 | Nt | 5–6 | 7–8 | 5 | Nt | Nt |
| J83PI12 | Nt | Nt | Nt | Nt | Nt | Nt |
| J83PI14 | Nt | 2 | 2 | 2 | Nt | Nt |
| J83PI17 | Nt | Nt | Nt | Nt | Nt | Nt |
| J83PI19 | Nt | 5–6 | 1–2 | 3 | 1–2 | 1–2 |
| J83PI11 | Nt | Nt | Nt | Nt | Nt | Nt |
| J83PI13 | Nt | 2–3 | 2–3 | 0 | Nt | Nt |

"Nt" means "not tested"

stood that various modifications can be made without departing from the spirit of the invention. Accordingly, the invention is limited only by the following claims.

What is claimed is:

1. A polynucleotide, comprising a sequence as set forth in SEQ ID NO:2.

2. A vector, comprising a sequence as set forth in SEQ ID NO:2.

3. The vector of claim 2, further comprising a restriction endonuclease restriction site in close proximity to SEQ ID NO:2.

4. An expression vector, comprising
a nucleic acid sequence encoding a gene product of interest, wherein a translation initiation start site for said gene of interest comprises sequence SEQ ID NO:2.

5. The expression vector of claim 4, wherein said gene product of interest comprises a selectable marker or a reporter.

6. The expression vector of claim 5, wherein said reporter is an enzymatic reporter or a fluorescent protein.

7. The expression vector of claim 5, wherein said reporter is beta-lactamase.

8. The expression vector of claim 4, wherein said vector is a plasmid.

9. The expression vector of claim 4, wherein said expression vector is a viral expression vector.

10. The expression vector of claim 9, wherein said expression vector is a retroviral expression vector.

11. The expression vector of claim 4, wherein said expression vector further comprises a promoter operably linked to said translation initiation start site.

12. The expression vector of claim 3, wherein said vector lacks a promoter.

13. The expression vector of claim 3, further comprising a splice donor sequence.

14. The expression vector of claim 12, further comprising a splice acceptor sequence.

15. A host cell, comprising the vector of claim 3.

16. The host cell of claim 15, wherein said host cell is a eukaryotic cell.

17. The host cell of claim 15, wherein said host cell is a prokaryotic cell.

18. A nucleic acid, comprising: a nucleic acid sequence encoding a selectable marker or reporter and a nucleic acid sequence encoding a translation initiation start site, wherein said translation initiation start site of said nucleic acid sequence comprises SEQ ID NO:2.

19. The nucleic acid of claim 18, wherein said reporter is an enzymatic reporter or a fluorescent protein.

20. The nucleic acid of claim 18, wherein said reporter is beta-lactamase.

* * * * *

UNITED STATES PATENT AND TRADEMARK OFFICE
CERTIFICATE OF CORRECTION

PATENT NO. : 6,107,477  Page 1 of 1
APPLICATION NO. : 09/167040
DATED : August 22, 2000
INVENTOR(S) : Michael A. Whitney It is certified that error appears in the above-identified patent and that said Letters Patent is hereby corrected as shown below:

On the Title page, column 1, item [22], please delete "October 6, 1998" and insert therin --October 5, 1998--.

Signed and Sealed this

Twenty-fourth Day of October, 2006

JON W. DUDAS
*Director of the United States Patent and Trademark Office*